(12) United States Patent
Zheng et al.

(10) Patent No.: US 6,804,553 B2
(45) Date of Patent: Oct. 12, 2004

(54) BACHMANN'S BUNDLE ELECTRODE FOR ATRIAL DEFIBRILLATION

(75) Inventors: Xiangsheng Zheng, Birmingham, AL (US); Michael E. Benser, Birmingham, AL (US); Raymond E. Ideker, Birmingham, AL (US); Gregory P. Walcott, Wilsonville, AL (US); Steven D. Girouard, Woodbury, MN (US)

(73) Assignee: The UAB Research Foundation, Birmingham, AL (US)

( * ) Notice: Subject to any disclaimer, the term of this patent is extended or adjusted under 35 U.S.C. 154(b) by 132 days.

(21) Appl. No.: 09/978,513

(22) Filed: Oct. 15, 2001

(65) Prior Publication Data

US 2002/0188326 A1 Dec. 12, 2002

Related U.S. Application Data

(63) Continuation-in-part of application No. 09/827,535, filed on Apr. 6, 2001.
(60) Provisional application No. 60/196,722, filed on Apr. 13, 2000.

(51) Int. Cl.$^7$ ................................................ A61N 1/39
(52) U.S. Cl. .......................................................... 607/5
(58) Field of Search ................................ 607/122–128, 607/5; 600/381, 374, 375

(56) References Cited

U.S. PATENT DOCUMENTS

| | | |
|---|---|---|
| 5,433,729 A | 7/1995 | Adams et al. |
| 5,476,499 A | 12/1995 | Hirschberg |
| 5,509,925 A | 4/1996 | Adams et al. |
| 5,630,834 A | 5/1997 | Bardy |
| 5,800,465 A | 9/1998 | Thompson et al. |
| 5,978,705 A | 11/1999 | KenKnight et al. |
| 6,178,351 B1 | 1/2001 | Mower |
| 6,345,204 B1 * | 2/2002 | Scheiner et al. ............ 607/123 |

OTHER PUBLICATIONS

International Search Report, International Application No. PCT/US01/11032.
Ideker, Raymond E., et al., *Current Concepts for Selecting the Location, Size and Shape of Defibrillation Electrodes*, PACE, vol. 14, Part 1, pp. 227–270 (Feb. 1991).

* cited by examiner

Primary Examiner—Jeffrey R. Jastrzab
(74) Attorney, Agent, or Firm—Myers Bigel Sibley & Sajovec

(57) ABSTRACT

An implantable system for the defibrillation of the atria of a patient's heart comprises (a) a first catheter configured for insertion into the right atrium of the heart; a first atrial defibrillation electrode carried by the first catheter and positioned to stimulate Bachmann's bundle, or positioned at the atrial septum of the heart (i.e., an atrial septum electrode); (b) a second atrial defibrillation electrode which together with the first atrial defibrillation electrode provides a pair of atrial defibrillation electrodes that are configured for orientation in or about the patient's heart to effect atrial defibrillation, and (c) a pulse generator operatively associated with the pair of atrial defibrillation electrodes for delivering a first atrial defibrillation pulse to the heart of the patient. The second electrode may be configured for positioning through the coronary sinus ostium and in the coronary sinus or a vein on the surface of the left ventricle, such as the great vein. An additional electrode configured for positioning in the superior vena cava, right atrium (including the right atrial appendage, or the right ventricle may also be included, and the pulse generator may be configured or programmed for concurrently delivering a first defibrillation pulse through the additional electrode and the atrial septum electrode, and a second defibrillation pulse through the atrial septum electrode and the second electrode. Electrode assemblies and methods useful for carrying out the invention are also disclosed.

22 Claims, 11 Drawing Sheets

BACHMANN'S BUNDLE ELECTRODE FOR ATRIAL DEFIBRILLATION

RELATED APPLICATIONS

This application is a continuation-in-part of U.S. patent application Ser. No. 09/827,535, filed Apr. 6, 2001, which in turn claims the benefit U.S. provisional application Ser. No. 60/196,722, filed Apr. 13, 2000, the disclosures of both of which are incorporated by reference herein in their entirety.

GOVERNMENT SUPPORT

This invention was made with Government support under National Institute of Health grant HL-42760. The Government has certain rights to this invention.

FIELD OF THE INVENTION

This invention relates to methods, apparatus, and catheters that may be used to administer a therapeutic electrical pulse, such as an atrial defibrillation pulse, to the heart of a patient in need of such treatment.

BACKGROUND OF THE INVENTION

Atrial fibrillation (AF) is the most common arrhythmia in humans and represents a significant public health problem. There are presently 2.2 million cases of AF in the United States and approximately 160,000 new cases diagnosed each year. AF is typically managed by a combination of anti-arrhythmic drugs and external or internal electrical cardioversion. In addition, surgical compartmentalization or radiofrequency ablation of atrial tissue can be used. Unfortunately, long term success rates are low; AF recurrence is high with both drug treatment and electrical cardioversion with internal and external shocks.

Internal electrical cardioversion of AF remains an uncomfortable therapy option for managing patients with AF. Even with recent advancements, shock voltages necessary to defibrillate the atrial, while considerably lower than that for the ventricles, are still beyond the pain threshhold. One reason high voltages may be necessary is that the main generator for AF is the left atrium and direct access to the left atrium is problematic because of the risk of embolism. Typically, atrial defibrillation lead locations are limited to right sided chambers (right atrium and right ventricle) and venous structures accessible from the right side of the heart (coronary sinus).

To create a trans-atrial shocking vector, the most common approach is to shock between one or more electrodes on the right side of the heart (right atrial appendage, superior vena cava, or right ventricle) to an electrode on the left side of the heart in the distal coronary sinus. The left atrium is also an important atrial chamber to defibrillate since (i) it can fibrillate independent of the right atrium, (ii) mapping studies have shown that earliest sites of activation following failed defibrillation arise from the left atrium for most defibrillation electrode configurations, (iii) early sites in or near the pulmonary veins have been shown to be responsible for the initiation of and early reoccurence of AF in many patients, and (iv) ablation of right atrial structures alone has had poor success in terminating AF or preventing its reoccurence. Nevertheless, there remains a need for means of defibrillating the atria of a subject without unduly high energy defibrillation pulses that would be painful to the subject being treated.

SUMMARY OF THE INVENTION

A first aspect of the present invention is an implantable system for the defibrillation of the atria of a patient's heart. The system comprises (a) a first catheter configured for insertion into the right atrium of the heart (in one embodiment preferably without extending into the right ventricle of the heart); a first atrial defibrillation electrode carried by the first catheter and positioned at Bachmann's bundle or at the atrial septum of the heart (i.e., a Bachmann's bundle or an atrial septum electrode); (b) a second atrial defibrillation electrode which together with the first atrial defibrillation electrode provides a pair of atrial defibrillation electrodes that are configured for orientation in or about the patient's heart to effect atrial defibrillation, and (c) a pulse generator operatively associated with the pair of atrial defibrillation electrodes for delivering a first atrial defibrillation pulse to the heart of the patient. The second electrode may be configured for positioning through the coronary sinus ostium and in the coronary sinus or a vein on the surface of the left ventricle, such as the great vein. As explained further below, an additional electrode configured for positioning in the superior vena cava, right atrium (including the right atrial appendage, or the right ventricle may also be included, and the pulse generator may be configured or programmed for concurrently delivering a first defibrillation pulse through the additional electrode and the atrial septum electrode, and a second defibrillation pulse through the atrial septum electrode and the second electrode.

A second aspect of the present invention is a catheter assembly useful for the defibrillation or cardioversion of a patient's heart. The assembly comprises: (a) a first transveneous catheter configured for insertion into the heart of the patient, the first transvenous catheter having a proximal end portion, a distal end portion, and an elongate intermediate portion therebetween, and with the first transveneous catheter having a first electrode connected thereto; (b) a second transveneous catheter configured for insertion into the heart of the patient, the second transveneous catheter having a proximal end portion, a distal end portion, and an elongate intermediate portion therebetween; and (c) a connecting member attached to the first transveneous catheter, with the connecting member connected to the second transveneous catheter intermediate portion.

A further aspect of the present invention is a method for the defibrillation or cardioversion of the heart of a patient in need thereof while minimizing or reducing the voltage of the defibrillation pulses to be delivered. The method comprises the steps of: (a) positioning first and second defibrillation electrodes in operable association with the heart of the subject, the first and second defibrillation electrodes defining a gradient field in the heart, the gradient field including a region of the heart to be defibrillated; (b) positioning a third electrode in the gradient field between the first and second electrodes; and then (c) concurrently delivering (i) a first defibrillation pulse between the first and third electrode and (ii) a second defibrillation pulse between the second and third electrodes; with the first and second defibrillation pulses together effective to defibrillate the heart. The voltage required for each of the first and second defibrillation pulses is preferably less than the voltage necessary for a single defibrillation pulse delivered between the first and second electrodes that is effective to defibrillate the heart. One, two or three or more additional electrodes may be positioned between the first, second and third electrodes to further reduce the voltage required, with additional shocks being delivered concurrently between various combinations of the electrodes (typically between adjacent electrodes).

A further aspect of the present invention is an implantable system for the defibrillation or cardioversion of a patient's heart. The system comprises: (a) first and second defibrillation electrodes configured for positioning in operable association with the heart of the subject, the first and second defibrillation electrodes when so positioned defining a gradient field in the heart between the first and second electrodes and in a region to be defibrillated; (b) a third defibrillation electrode configured for positioning in the gradient field between the first and second electrodes; and (c) a pulse generator operatively associated with the first, second and third defibrillation electrodes and configured for concurrently delivering (a) a first defibrillation pulse between the first and third electrode and (b) a second defibrillation pulse between the second and third electrodes. The two pulses are together effective to defibrillate the heart. Preferably, the voltage required for each of the first and second defibrillation pulses is less than the voltage required for a single defibrillation pulse delivered between the first and second electrodes that is effective to defibrillate the heart. Such an apparatus may be configured to carry out the methods described above.

In preferred embodiments of the foregoing methods and systems, there is further provided first and second transveneous catheters, wherein the first, second and third electrodes are carried by the first and second transveneous catheters, and wherein the first transveneous catheter is fixed to the second transveneous catheter.

In particularly preferred embodiments of the foregoing methods and systems, the first and second electrodes are carried by a first transveneous catheter, the first transveneous catheter having a proximal end portion, a distal end portion, and an elongate intermediate portion therebetween. The third electrode is carried by a second transveneous catheter, the second transveneous catheter having a proximal end portion, a distal end portion, and an elongate intermediate portion therebetween. The second transveneous catheter distal end portion is connected to the first transveneous catheter intermediate portion through a connecting member, as described in connection with catheter assemblies above. The third electrode is then, preferably, an atrial septum electrode.

A further aspect of the present invention is an implantable system for the electrical treatment/defibrillation of the atria of a patient's heart, the system comprising: a first atrial therapeutic electrode configured for stimulating Bachmann's bundle and for positioning on or adjacent Bachmann's bundle along the superior aspect of the atrium and adjacent to the atrial septum; a second atrial electrode which together with the first atrial electrode provides a pair of atrial electrodes; and a pulse generator operatively associated with the pair of atrial electrodes for delivering an atrial defibrillation or other therapeutic pulse. Methods of delivering an atrial defibrillation pulse, or other therapeutic pulse, by positioning electrodes as described above are a further aspect of the invention. The first atrial electrode may be carried by a first catheter, with the first catheter configured for insertion into the right atrium of the heart, preferably without extending into the right ventricle of the heart. The second atrial electrodes may be positioned as described in connection with second electrodes corresponding to or paired with atrial septum electrodes as described herein.

A further aspect of the present invention is a method for the electrical treatment or defibrillation of the atria of a patient's heart, comprising the steps of: providing a set of atrial therapeutic electrodes for defibrillating the patient's heart, or otherwise administering a therapeutic electric pulse to the patients heart, the set including a first atrial electrode positioned in the superior vena cava of the patient; delivering a first therapeutic electric pulse such as a defibrillation pulse to the atria of the heart, and then delivering a second therapeutic electric pulse such as a defibrillation pulse pulse to the atria of the heart, wherein at least one of the first and second pulses is delivered with the first atrial defibrillation electrode. Sets of atrial therapeutic or defibrillation electrodes that may be used to carry out this method include but are not limited to the sets of atrial defibrillation electrodes described herein. For example, the set of atrial electrodes may further comprise a second atrial therapeutic or defibrillation electrode positioned in the coronary sinus of the heart, and at least one of the first and second pulses may be delivered with the second atrial electrode. In one embodiment, at least one of the first and second therapeutic pulses is delivered between the first and second therapeutic electrodes.

A further aspect of the present invention involves the balancing of peak amplitudes for defibrillating the atria or ventricles of a patient's heart, or otherwise delivering a therapeutic electric pulse to the atria or ventricles of a patient's heart. The method comprises: delivering a first therapeutic electrical pulse such as a defibrillation pulse to the atria or ventricles of the heart, and then delivering a second therapeutic electric pulse such as a defibrillation pulse to the atria or ventricles of the heart, wherein the total energy, or leading edge peak voltage, of the second pulse is at least 90 or 95% of the total energy, or leading edge peak voltage, of the first pulse. Sets of treatment electrodes that may be used to carry out this method include but are not limited to the sets of atrial treatment electrodes described herein. An apparatus configured to carry out this method (e.g., employing two separate discharge capacitors operatively associated with a power supply and a controller, with the controller configured so that the first capacitor is discharged by the controller to administer the first pulse and the second capacitor is discharged by the controller to administer the second pulse; or with a single capacitor having sufficient storage capacity so that the aforesaid energy or voltage features can be achieved through wave shaping through the controller) is a further aspect of the invention.

A still further aspect of the present invention is a transveneous catheter for stimulating the heart of a patient at separate locations therein, the catheter comprising: a catheter body having a proximal portion, an intermediate portion and a distal portion; a first electrode connected to the catheter body distal portion; a catheter appendage having a proximal portion and a distal portion, the appendage proximal portion connected to the catheter body intermediate portion; and a second electrode connected to the appendage distal portion. In one embodiment of the foregoing, the catheter body is configured for insertion into the right ventricle of the heart. In a particular embodiment of the foregoing, the catheter body is configured for insertion through the coronary sinus ostium and into the coronary sinus of the heart. The second electrode of the catheter may be an aterial electrode, such as an atrial septum electrode or a Bachmann's bundle electrode.

The foregoing and other objects and aspects of the present invention are explained in greater detail in the drawings herein and the specification set forth below.

DETAILED DESCRIPTION OF THE PREFERRED EMBODIMENTS

Figure 1:
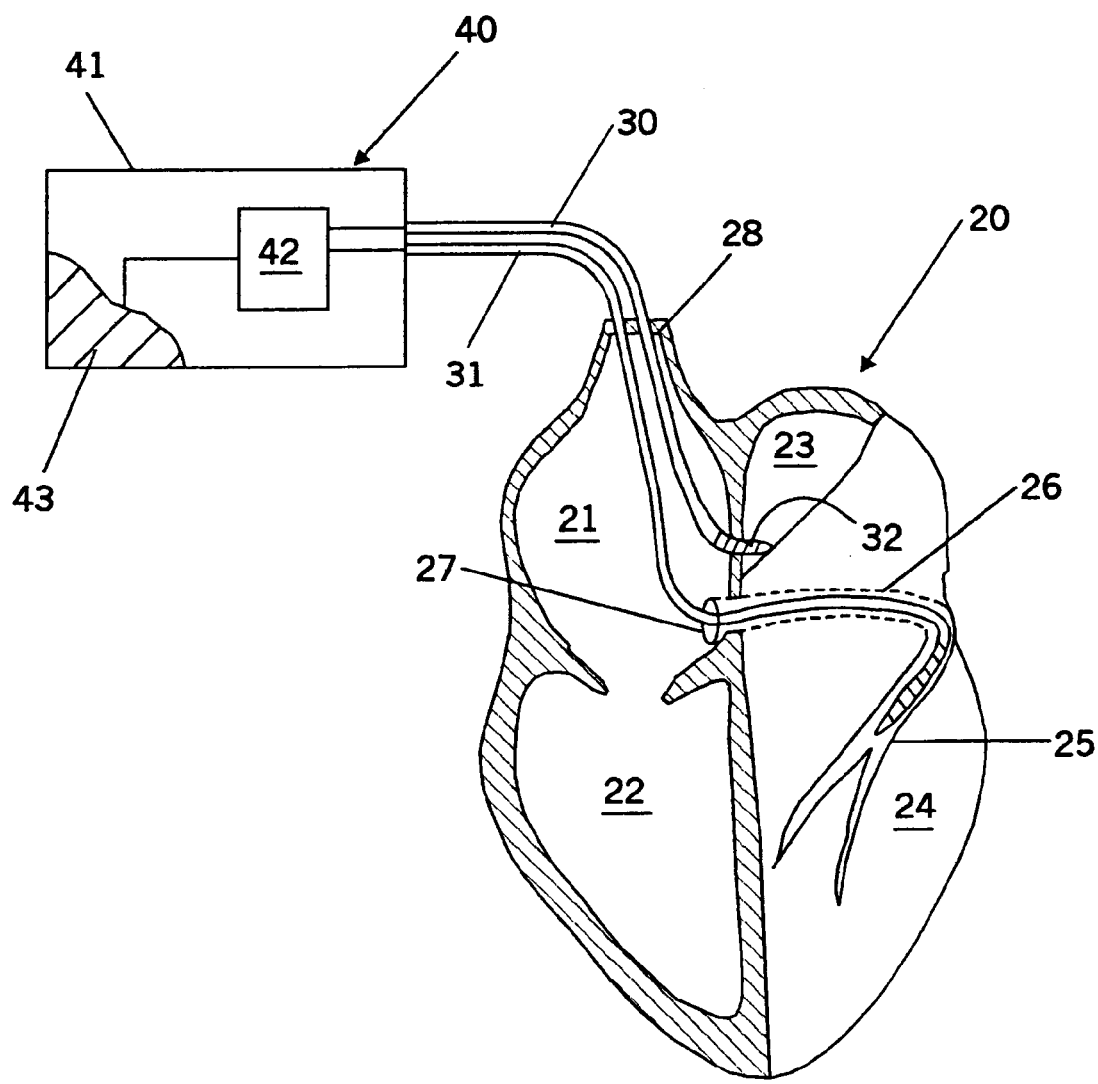
FIG. 1 illustrates a first embodiment of an implantable system of the present invention, in which the atrial septum electrode is a trans-septal electrode. The heart is shown in partial cut-away view, with the right atrium, the right ventricle, and a portion of the left atrium being shown in cross section. The surface of the left ventricle is shown so that vessels on the surface of the ventricle that are accessed through the coronary sinus (shown in dashed lines) may be seen.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

The terms "atrial septum electrode" or electrode positioned "at the atrial septum", as used herein, refer to an electrode that is, or is configured to be, inserted through the atrial septum (i. e., a trans-septal electrode), inserted into the atrial septum (i.e., inserted partially into the septum without penetrating completely through the septum), or substantially contacted to the surface of the atrial septum (typically the surface facing the right atrium). An atrial septum electrode may also be an electrode that is directly or indirectly secured to the atrial septum, but is spaced up to about 1, 2, or 4 millimeters or more away from the septum, where the electric field produced from the electrode is effective in stimulating the atrial septum in substantially the same manner as an electrode inserted into or contacting to the atrial septum. Patients treated by the methods of the present invention are typically human.

"Bachmann's bundle" as used herein refers to a transverse band of muscle fibers on the roof of the atria, immediately adjacent to or lying along side of the atrial septum.

The term "catheter" is used interchangeably with "lead" herein, and is not meant to imply that the particular structure has an interior lumen for receiving a guide wire or the like, as such a lumen is optional in carrying out the present invention, and the use of one or more guidewires is optional in carrying out the present invention.

The term "concurrently", when used herein with respect to two or more defibrillation pulses, refers to pulses that are administered sufficiently close in time so that the combined therapeutic effect is greater than the sum of the therapeutic effects when the pulses are administered singly. Such pulses may be administered simultaneously, partially overlapping in time, or sequentially in time. When administered sequentially in time the pulses may or may not have an intervening time period therebetween. Preferably, the onset of a subsequent pulse occurs within 100, 200 or 500 milliseconds of the offset of a preceding pulse.

The term "defibrillation pulse" is used herein to encompass any of a variety of defibrillation, or cardioversion, waveforms. The particular type of pulse delivered is not critical and may, for example, comprise: a monophasic or biphasic waveform; a pulse that includes a series of waveforms; waveforms that are uniform, stepped, saw-toothed, truncated exponential, etc.

The term "pulse generator" as used herein is intended to encompass any type of device, preferably contained within an implantable housing to form an implantable cardioverter defibrillator (ICD), that delivers the defibrillation pulse or pulses desired to achieve a particular method. In general, such pulse generators comprise a battery power supply, a control circuit, and a capacitor (or capacitor circuit). The control circuit is connected to the battery and the capacitor for charging the capacitor and delivering a therapeutic defibrillation pulse from the capacitor through the defibrillation electrodes. The control circuit typically includes a detection circuit for monitoring the heart of a subject and determining when the capacitor should be charged and a therapeutic pulse delivered. Numerous additional features may be included, as is known to those skilled in the art.

A. Atrial Septum Electrodes for Atrial Defibrillation

As noted above, the present invention provides an implantable system for the defibrillation of the atria of a patient's heart. Such a system typically comprises a first catheter configured for insertion into the right atrium of the heart; a first atrial defibrillation electrode carried by the first catheter and positioned at the atrial septum of the heart; a second atrial defibrillation electrode which together with the first atrial defibrillation electrode provides a pair of atrial defibrillation electrodes that are configured for orientation in or about the patient's heart to effect atrial defibrillation, and a pulse generator operatively associated with the pair of atrial defibrillation electrodes for delivering a first atrial defibrillation pulse to the heart of the patient. It will be appreciated that the atrial septum electrode need not be used in conjunction with every pulse or shock delivered by the system and methods as long as it used in some of the pulses or shocks delivered by the system and methods.

FIG. 1 illustrates a first embodiment of an implantable system of the present invention. The heart 20 is shown in partial cut-away view, with the right atrium 21, the right ventricle 22, and a portion of the left atrium 23 being shown in cross section. The surface of the left ventricle 24 is shown so that veins or vessels 25 on the surface of the ventricle that are accessed through the coronary sinus 26 (shown in dashed lines) and the coronary sinus ostium 27 may be seen. A pair of catheters 30, 31, enter the heart through the superior vena cava 28. One catheter is positioned through a trans-septal puncture formed in the atrial septum so that the atrial septal electrode 32 that is connected to that catheter extends through the septum. An introducer sheath, needle, or the like may be used to form the puncture and introduce the electrode therethrough, as will be apparent to those skilled in the art. The other catheter extends through the ostium of the coronary sinus and through the coronary sinus and into a vessel on the surface of the left ventricle of the heart (e.g., the great vein), where an additional defibrillation electrode 33 connected to that catheter is positioned.

The system includes an implantable cardioverter defibrillator (ICD) 40 comprises a housing 41 containing a pulse generator 42, with a subcutaneous electrode 43 located on the external surface of the housing as described in U.S. Pat. No. 5,292,338 to Bardy. The defibrillator is then implanted in the left or right (preferably left) thoracic region of the patient (e.g., subcutaneously, in the left pectoral region, in accordance with known techniques. The housing electrode 43 may be used in conjunction with or in alternative to other catheter mounted electrodes.

Sensing of atrial fibrillation for triggering of a defibrillation can be carried out through any suitable means, and may employ the same electrodes that are used for defibrillation or separate sensing electrodes. In the alternative, the defibrillation pulse may, if desired, be triggered manually or externally by an operator or the patient. It will be appreciated that a sensing electrode (not shown) will also preferably be provided in the right ventricle, e.g. on a separate catheter, to sense the ventricular cycles and deliver this information to the pulse generator so that the pulse generator delivers the atrial defibrillation pulse or pulses at a time when ventricular fibrillation is not likely to be induced thereby, as is known in the art.

While the atrial septum electrode is primarily described herein for the delivery of atrial defibrillation or cardioversion pulses, it will be appreciated that the system can be configured to carry out other useful methods from the atrial septum electrode. For example, an atrial septum electrode can be used to deliver pacing pulses from the pulse generator prior to the onset of atrial fibrillation to reduce the chance of atrial fibrillation occuring. In addition, an atrial septum electrode can be used to deliver pacing pulses after the onset of atrial fibrillation, but before a defibrillation pulse is delivered, in an effort to avoid the need to deliver a defibrillation pulse. If fibrillation continues after the pacing pulse is delivered, then a defibrillation pulse can be delivered. The atrial septum electrode used to deliver such pacing pulses may be the same or different from the atrial septum electrode used to deliver defibrillation pulses (e.g., multiple adjacent atrial septum electrodes may be provided on a single catheter).

Figure 2:
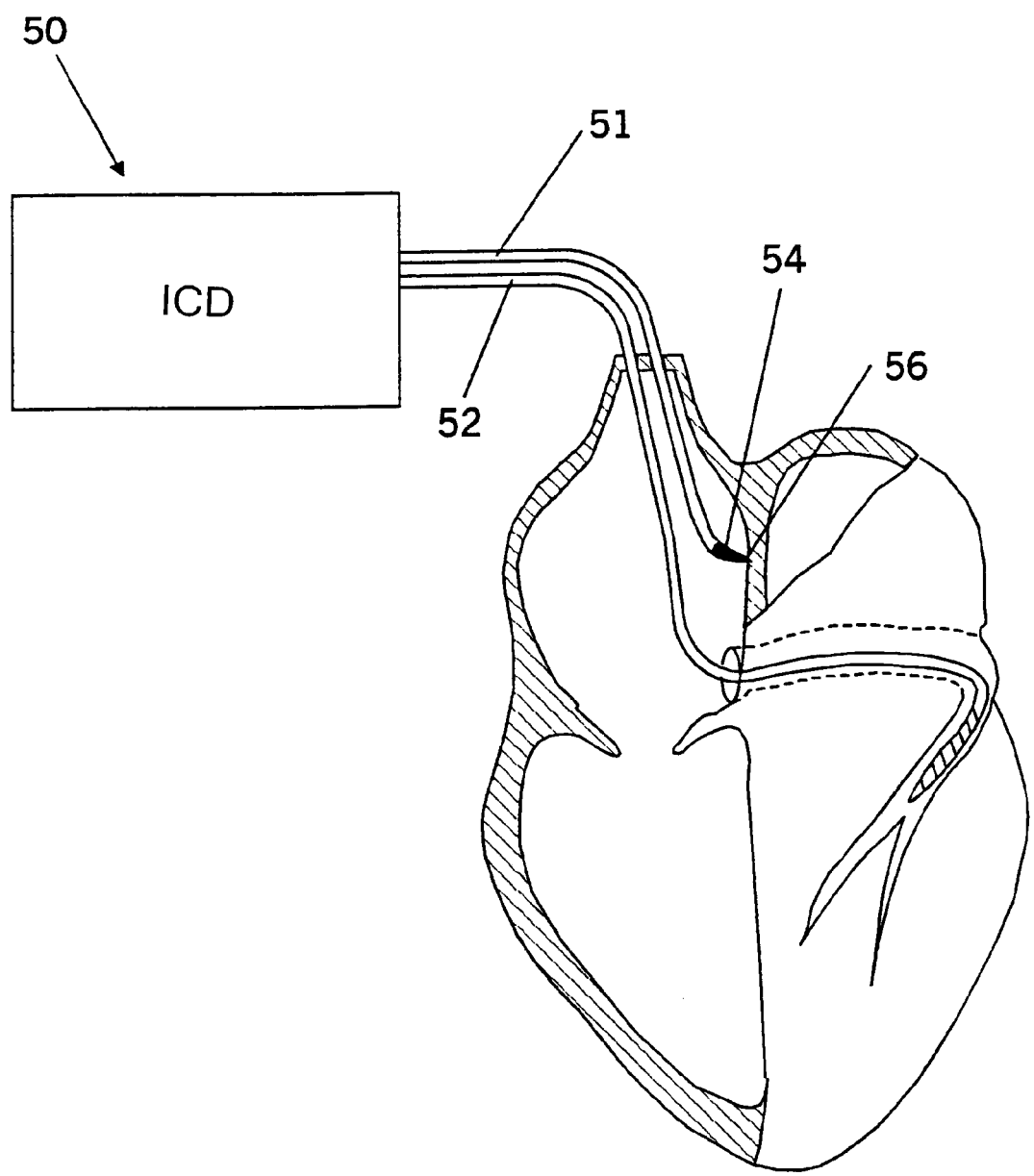
FIG. 2 illustrates a second embodiment of an implantable system of the present invention, in which the atrial septum electrode is fixed to the atrial septum by means of a terminal screw.

FIG. 2 illustrates a second embodiment of an implantable system of the present invention. This system again comprises an implantable ICD 50, a pair of catheters 51, 52, an atrial septum defibrillation electrode 54, and an additional defibrillation electrode 55 in the great vein. The atrial septum electrode is fixed to the atrial septum by a terminal screw or helix 56 connected to the distal end portion of catheter 51, which penetrates partially into (or all the way through) the atrial septum. Of course, any suitable connecting means may be employed in addition to a terminal screw or helix, including but not limited to a retractable hook connected to the distal end portion of the catheter 51.

Figure 3:
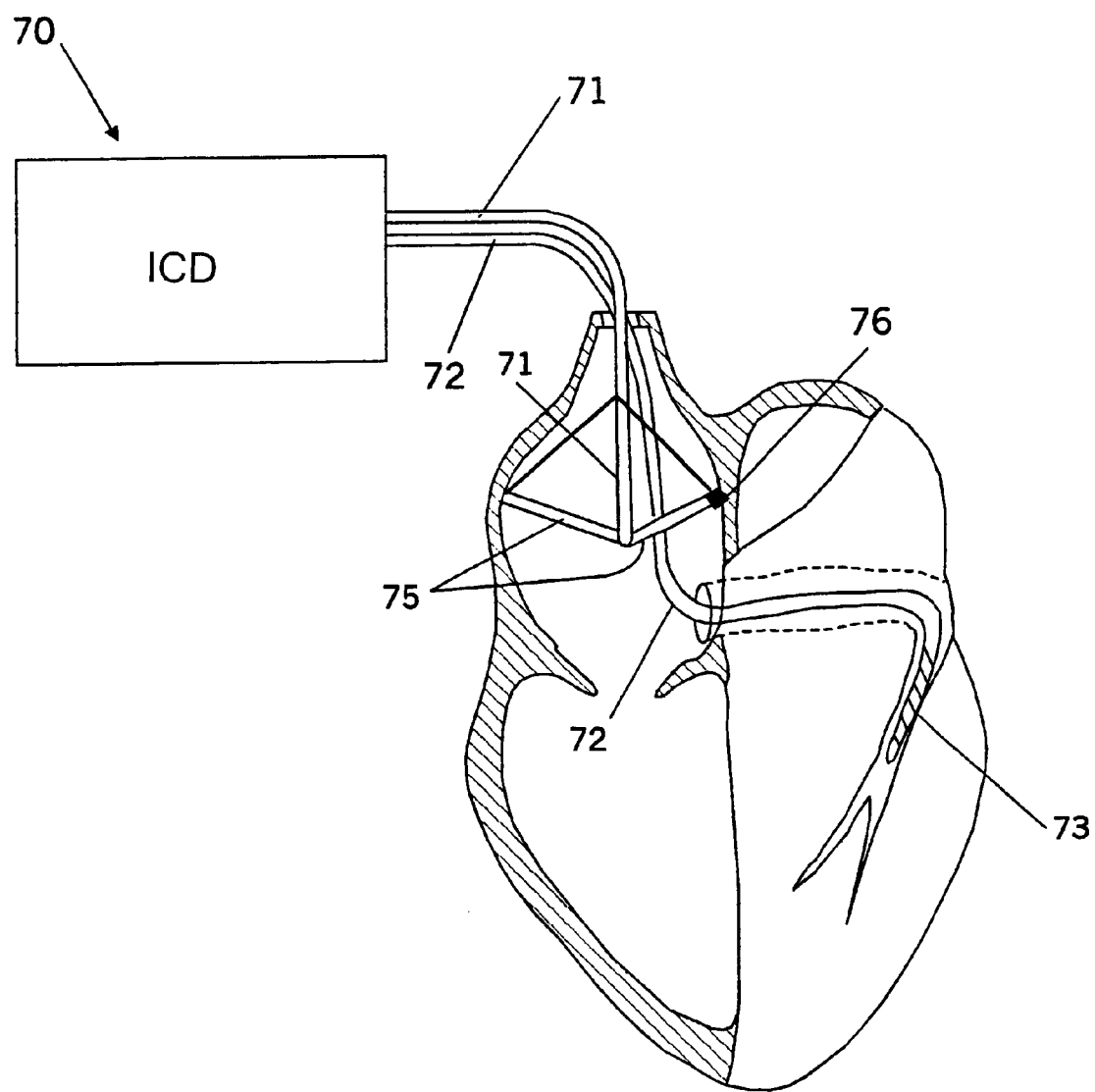
FIG. 3 illustrates a third embodiment of an implantable system of the present invention, in which the atrial septum electrode is incorporated into an expandable umbrella device which is opened within the right atrium to hold the electrode against the atrial septum.

FIG. 3 illustrates a third embodiment of an implantable system of the present invention, again including an implantable ICD 70, a pair of catheters 71, 72, and a defibrillation electrode 73 positioned in the great vein. The atrial septum electrode 74 is incorporated into an expandable device or element 75 which is opened within the right atrium (or allowed to open within the atrium by removal of an introducer sheath or the like) to hold the electrode 76 against the atrial septum by expanding to a size about the same as or slightly greater than the interior diameter of the right atrium and forcing the electrode against the atrial septum. In the alternative, an expandable element could be used in conjunction with a helix, screw, hook or other fixing means located on the distal tip of the catheter to unfold the electrode into a configuration contacting the atrial septum, to thereby provide better contact or expanded contact area of the defibrillation electrode against the atrial septum.

Figure 4:
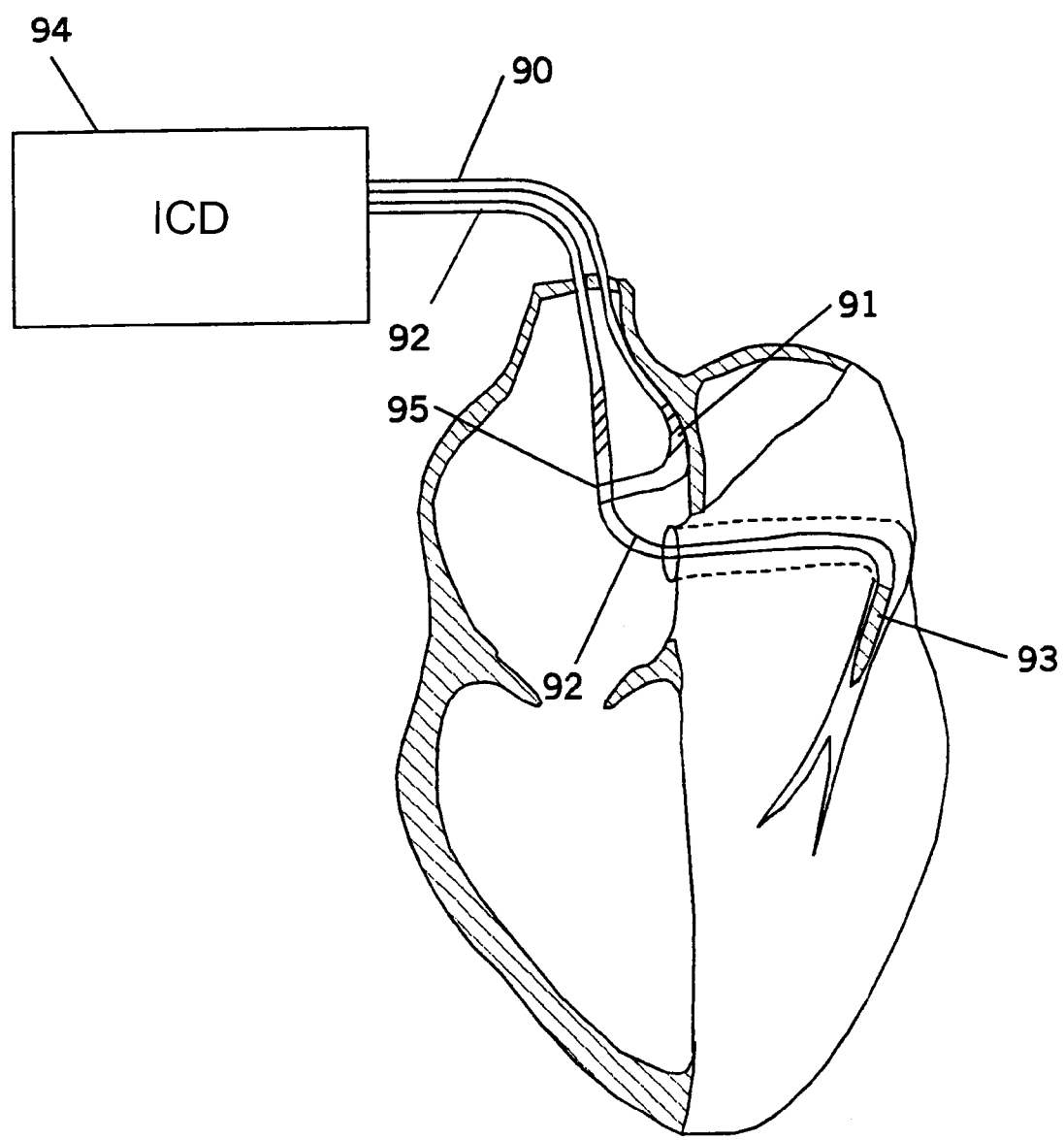
FIG. 4 illustrates a fourth embodiment of an implantable system of the present invention, in which the atrial septum electrode is fixed to the coronary sinus electrode to form a catheter assembly and facilitate the holding of the atrial septum electrode against the atrial septum.

FIG. 4 illustrates a particularly preferred embodiment of an implantable system of the present invention, in which the catheter 90 carrying the atrial septum electrode 91 is fixed to the catheter 92 carrying coronary sinus electrode 93 to form a catheter assembly and facilitate the holding of the atrial septum electrode against the atrial septum. The system includes an ICD 94, which again may incorporate features such as described in connection with ICDs as set forth above. A connecting member 95, typically located at the distal end portion of the first catheter and connected to the intermediate portion of the second catheter, is included for interconnecting the two catheters. Such a configuration or assembly, in addition to being particularly suitable for carrying out the present invention has a variety of different applications, and is discussed in greater detail in section B below.

B. Catheter Assembly with Fixation of One Catheter to Another

The present invention provides a catheter assembly useful for the defibrillation or cardioversion of a patient's heart, of which the assembly illustrated in FIG. 4 is one example. As noted above, such assemblies typically comprise a first transveneous catheter configured for insertion into the heart of the patient, the first transvenous catheter having a proximal end portion, a distal end portion, and an elongate intermediate portion therebetween. The first transveneous catheter typically has a first electrode connected thereto. The first electrode is typically connected to the first transveneous catheter intermediate portion, although it will be noted that the intermediate portion is quite elongate and the first electrode may be positioned anywhere along the length thereof.

A second transveneous catheter configured for insertion into the heart of the patient is also included in the assembly, the second transveneous catheter also having a proximal end portion, a distal end portion, and an elongate intermediate portion therebetween. The second catheter may, for example, be configured for positioning in a suitable location, such as into the right ventricle, optionally extending to the apex of the right ventricle, through the ostium of the coronary sinus and into or through the coronary sinus, etc. The assembly further includes a connecting member attached to the first transveneous catheter (e.g., at the distal end portion or at the proximal portion thereof), with the connecting member connected to the second transveneous catheter intermediate portion.

The second transveneous catheter generally has at least one electrode connected thereto (. e.g., an electrode for positioning in the coronary sinus or a vein on the surface of the left ventricle), which electrode may be a therapeutic, or defibrillation, electrode, and/or a monitoring electrode such as a ring electrode or tip electrode. However, the second transveneous catheter need not necessarily carry an electrode if it functions primarily to secure or anchor the first catheter in place. Hence, the second catheter may be referred to as an "anchoring catheter" or "positioning catheter".

While such catheter assemblies may be used for atrial defibrillation systems and methods as described herein, it is also envisioned that such catheter assemblies will find a variety of additional applications, such as for ventricular defibrillation or cardioiversion, whenever it is desirable to securely fix a particular catheter in place.

Figure 5:
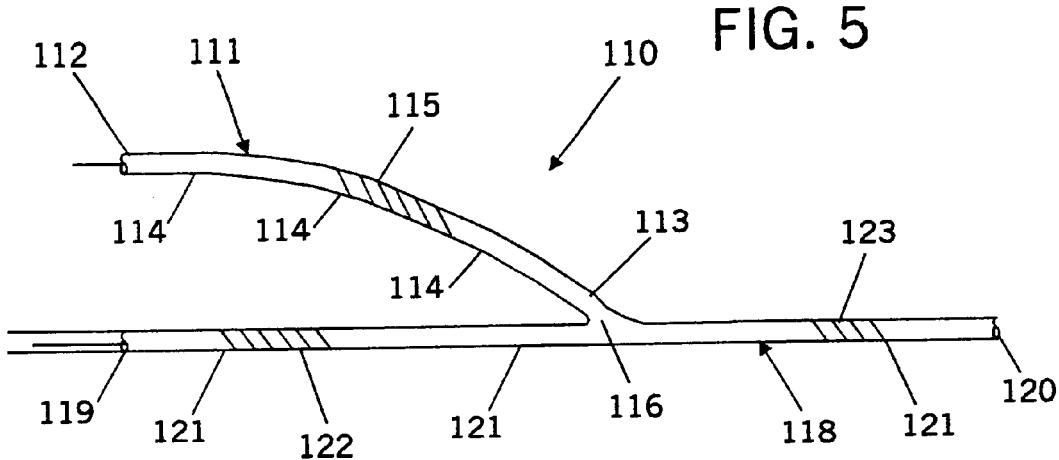
FIG. 5 illustrates a catheter assembly as used in FIG. 4, in which the first catheter is permanently fixed to the second catheter.

FIG. 5 illustrates a catheter assembly 110 of the present invention, which may be configured in any suitable manner including but not limited to that shown in FIG. 4. The assembly comprises a first catheter 111 having a proximal end portion, 112, a distal end portion 113, and an elongate intermediate portion 114 therebetween. Note that proximal end portions will typically terminate in a connector (not shown) to facilitate mechanical connection of the catheters to the ICD and electrical connection of the electrodes to the pulse generator contained therein. A first defibrillation electrode 115 is connected to the intermediate portion 114. A connecting member 116 is connected to the distal end portion 113 of the first catheter, and is permanently fixed to the second catheter 118 (e.g, by permanently fastening two separate members; by integrally forming the two members together). Second catheter 118 also has a proximal end portion 119, a distal end portion 120, and an intermediate portion 121, with a defibrillation electrode 122 positioned proximal to the connecting member and a further defibrillation electrode 123 positioned distal to the connecting member. As noted above, either or both of the electrodes on the second catheter are optional, and additional electrodes such as sensing electrodes could be included if desired.

Figure 6:
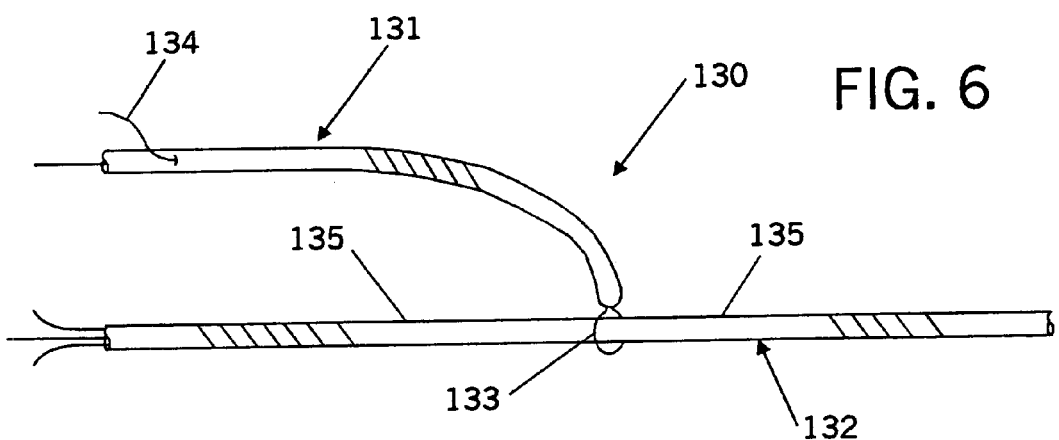
FIG. 6 illustrates an alternate embodiment of a catheter assembly of the present invention, in which the first catheter is releasably fixed to the second catheter by means of a retractable loop.

FIG. 6 illustrates an alternate embodiment of a catheter assembly 130 of the present invention, in which the first catheter 131 is releasably fixed to second catheter 132 by means of a retractable loop 133. Any suitable means can be used to retract the loop, such as the insertion of a tendon 134 through a lumen in catheter 131 which connects to the loop, and which can be drawn back to tighten the loop. As with any other such releasably secured connecting member, the loop can be fastened around an intermediate portion 135 of the catheter assembly at any of a variety of locations to optimally configure the electrode assembly for a particular patient. The intermediate portion 135 can be substantially smooth as illustrated, or may be textured or the like to enhance fastening of the loop to the catheter and reduce lateral slippage along the length of the second catheter intermediate portion. If desired, an introducer sheath (not shown) can be deployed around the second catheter and used to push the loop forward down the second catheter until the desired location is achieved (e.g., just outside or proximal to the coronary sinus ostium, when the second catheter is inserted through the ostium), with the loop then being tightened and the introducer sheath removed. In the alternative, an introducer can be used to carry the second catheter to the desired position rather than push the connecting member to the desired position.

Figure 7:
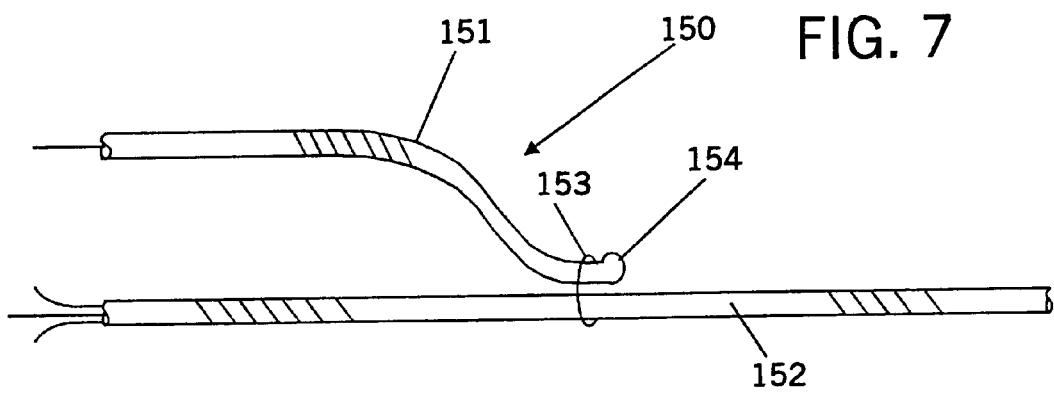
FIG. 7 illustrates a further alternate embodiment of a catheter assembly of the present invention, in which the first catheter is releasably fixed to the second catheter by means of an elastic loop.

FIG. 7 illustrates a further alternate embodiment of a catheter assembly 150 of the present invention, in which the first catheter 151 is releasably fixed to the second catheter 152 by means of an elastic loop 153. The elastic loop may be formed of any suitable polymeric material, metallic material or the like that is sufficiently resilient to allow its deformation and reformation around the second catheter (and, if necessary, around the first catheter). The distal end portion 154 of the first catheter is enlarged to reduce the chance of the resilient loop slipping off the tip thereof (or, in the alternative or in addition thereto, the resilient loop could be permanently fastened to the first catheter). As in the embodiment of FIG. 6, an introducer sheath may be deployed around the second catheter to push the elastic loop to the proper location around the second catheter. Again, texturing or the like could be provided on the intermediate portion of the second catheter to reduce slippage along the length thereof.

In a variation to the embodiment described above in connection with FIG. 7, the fastening loop 153 could be substantially inelastic, if the second and/or first catheter itself were sufficiently elastic to allow the catheter to be forced therethrough, yet sufficiently resilient to secure the catheters to the loop when forced to the desired location by means of an introducer sheath or the like.

Figure 8:
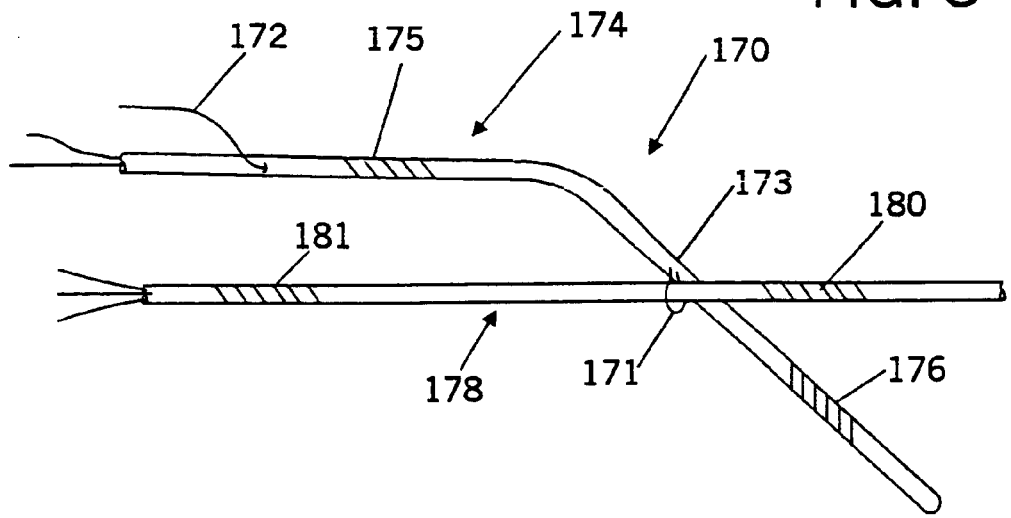
FIG. 8 illustrates a still further alternate embodiment of a catheter assembly of the present invention, in which the connecting member is positioned on an intermediate portion rather than the distal portion of the first catheter.

FIG. 8 illustrates a still further embodiment of a catheter assembly 170 of the present invention, in which the connecting member (a retractable loop 171 with a tendon 172 as illustrated) is positioned on an intermediate portion 173 of the first catheter 174 rather than the distal portion of the first catheter as shown above. Any number of electrodes could be included in such an embodiment. As illustrated, the first catheter 174 has electrodes 175, 176 proximal and distal to the connector, and the second catheter 178 has electrodes 180, 181 proximal and distal to the loop connector. Such an assembly could be used, for example, to position electrode 180 in or through the coronary sinus, electrode 176 in the right ventricle, electrode 175 at the atrial septum, and electrode 181 in the right atrium or superior vena cava.

Figure 9:
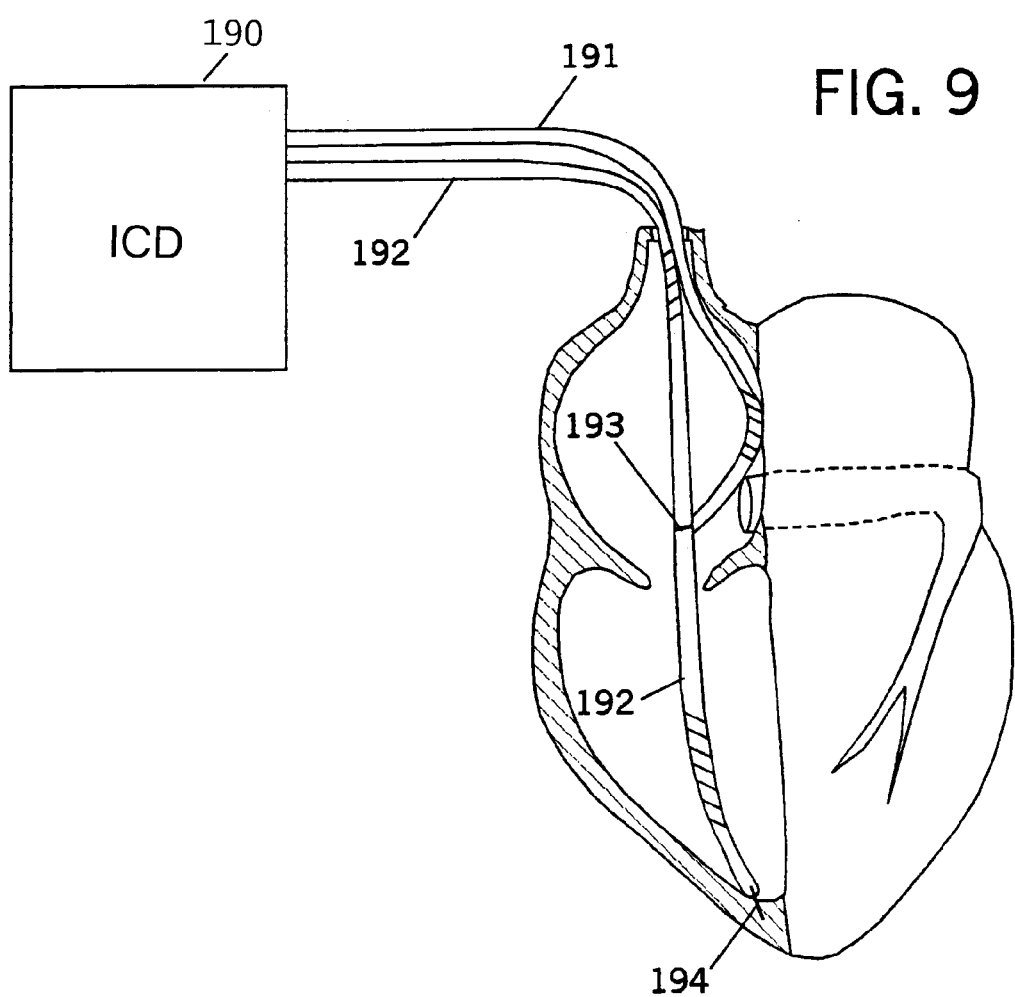
FIG. 9 illustrates a still further alternate embodiment of an implantable system incorporating a catheter assembly of the present invention, in which the second catheter extends into the right ventricle and is fixed to the apex of the right ventricle by means of a terminal screw.

FIG. 9 illustrates a still further alternate embodiment of an implantable system comprising an ICD 190, and a pair of catheters 191, 192 configured as an assembly through a connector 193. Here the second catheter extends into the right ventricle and is fixed to the apex of the right ventricle by means of a terminal screw or helix 194. Any other terminal fastening means, such as a retractable hook, could also be employed.

Figure 10:
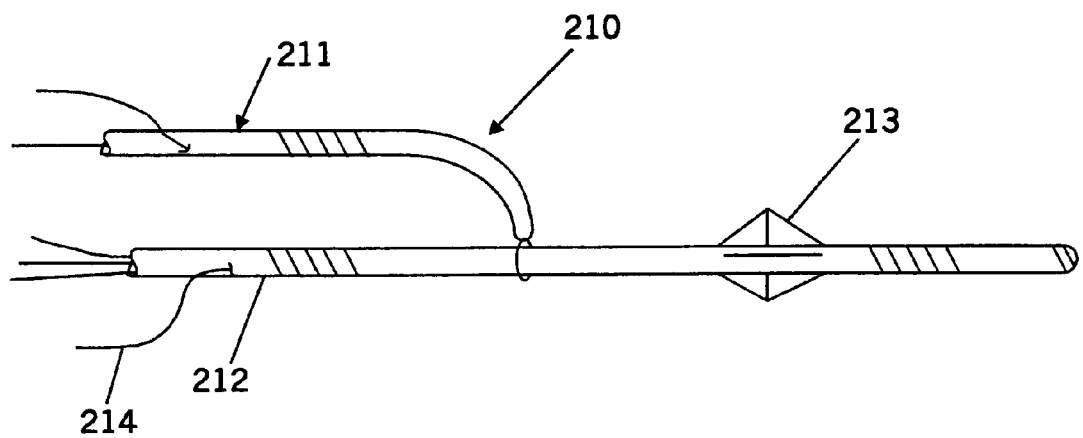
FIG. 10 illustrates a further embodiment of a catheter assembly of the present invention, in which the second catheter includes an expandable stent to further anchor the second catheter within a suitable vessel, such as a pulmonary artery.

FIG. 10 illustrates a further embodiment of a catheter assembly 210 of the present invention, comprising first and second catheters 211, 212, and in which the second catheter includes an expandable stent 213 that is expanded or retracted by tendon 214 to further anchor the second catheter within a suitable vessel, such as a pulmonary artery. Such an additional anchoring feature could be added as appropriate to any of the embodiments described above.

C. Location of Additional Electrodes to Lower Shock Voltage and Energy Required for Defibrillation A further aspect of the present invention is a method for the defibrillation or cardioversion of the heart of a patient in need thereof while minimizing the voltage of defibrillation pulses to be delivered. As noted above, the method involves, first, positioning first and second defibrillation electrodes in operable association with the heart of the subject, the first and second defibrillation electrodes defining a gradient field in the heart, the gradient field including a region of the heart to be defibrillated. Next, a third electrode (e.g., an atrial septum electrode) is positioned in the gradient field between the first and second electrodes. Then, a first defibrillation pulse between the first and third electrode and a second defibrillation pulse between the second and third electrodes are concurrently delivered, with the first and second defibrillation pulses together effective to defibrillate the heart. The voltage required for each of the first and second defibrillation pulses is preferably less than the voltage necessary for a single defibrillation pulse delivered between the first and second electrodes that is effective to defibrillate the heart. All of the electrodes may be carried on transveneous catheters, either separately or with multiple electrodes on a single catheter.

Such a technique can be used for any of a variety of purposes, including treating patients afflicted with atrial fibrillation and patients afflicted with ventricular fibrillation. For atrial fibrillation, each of the first and second defibrillation pulses are preferably not greater than, and more preferably less than, 50, 100, or 150 volts in magnitude, and each of the first and second defibrillation pulses are preferably not greater than, and more preferably less than, one, two or four Joules in magnitude. Preferably, the gradient field created by the first defibrillation pulse and the second defibrillation pulse in the region of the heart to be defibrillated is at least 3 or 4 volts per centimeter. The specific minimum potential gradient (which must be created throughout all, or substantially all, of the fibrillating myocardium), differs for different defibrillation waveforms, but is thought to be in the range of approximatley 4 to 7 volts per centimeter, with at least about a 4 volt per centimeter gradient needed for a good biphasic defibrillation waveform.

Figure 11A:
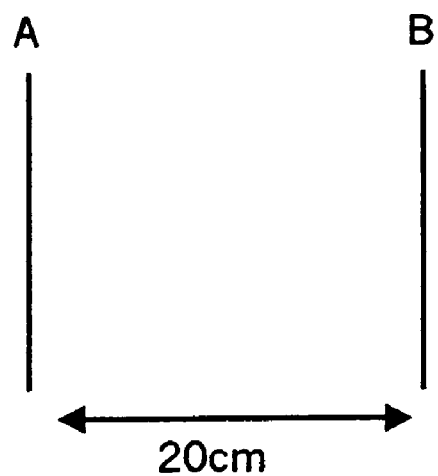
FIGS. 11A–C schematically illustrate a technique for lowering shock voltage that may be used in conjunction with the instant invention or other defibrillation techniques.
Figure 11B:
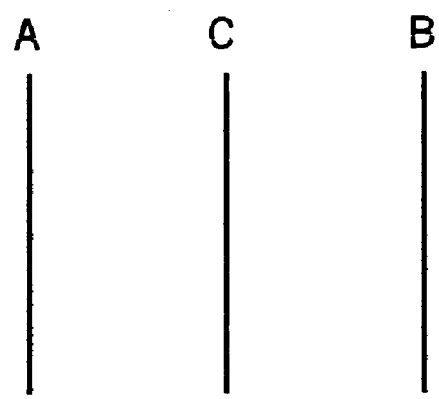
Figure 11C:
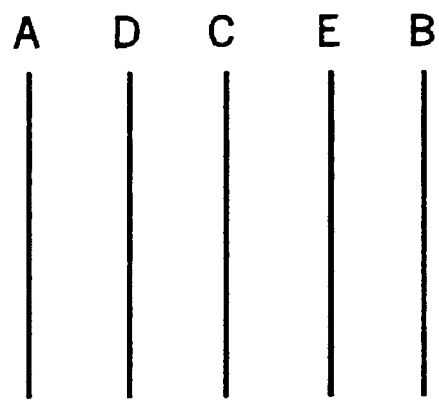

FIGS. 11A–C schematically illustrates such a technique. Panel A illustrates an original pair of electrodes (A and B) that create a substantially even potential gradient field in the region between the two electrodes, with the gradient field including a region in the atria or ventricles or the heart of a patient to be defibrillated. Assuming that (1) the electrodes are 20 cm apart, (2) the conductivity of the medium is substantially uniform, and (3) there is no substantial voltage loss at the electrode-media interface, and (4) a 4 volt per centimeter potential gradient must be created throughout the region, then a shock voltage of about 80 volts will be required. Panel B shows a third electrode (C) approximately half way between the original pair of electrodes (A,B). A shock between electrodes A and C will create a potential gradient of 4 volts per centimeter in the left half of the region with a 40 volt shock. Similarly, a 40 volt shock between electrodes C and B will create the desired 4 volt per centimeter potential gradient throughout the right half of the region. If the two shocks are given concurrently and are substantially the same duration as the original shock through electrodes A and B, then the voltage of each shock will be approximately half that of the original, while the total energy of the two shocks will be the same as that of the original shock. Therefore, the maximum voltage delivered to the heart of the patient in this example will be about 40 volts rather than 80 volts.

More than three electrodes may be used to implement this technique. For example, panel C of FIG. 11 shows the addition of two additional electrodes (D and E). Concurrent (e.g., sequential) shocks through four pairs of electrodes (A to D, D to C, C to E, and E to B) in various sequences will again reduce the voltage in half to 20 volts while maintaining the same total energy.

When this technique is used for atrial defibrillation, such as with a system and/or catheter assembly as illustrated in connection with FIGS. 1–10 above, the method may comprise the steps of: (a) positioning a first defibrillation electrode in the right atrium (including the right atrial appendage), superior vena cava or right ventricle of the subject; (b) positioning a second defibrillation electrode in the coronary sinus or a vein on the surface of the left ventricle of the heart (e.g., the great vein); (c) positioning a third electrode at the atrial septum of the heart; and then (d) concurrently delivering (i) a first defibrillation pulse between the first and third electrode and (ii) a second defibrillation pulse between the second and third electrodes. Preferably, each of the first and second defibrillation pulses has an energy not greater than, or less than, one, two or four Joules, preferably each of the first and second defibrillation pulses has a voltage less than 50, 100 or 150 volts, preferably the first and second defibrillation pulses are delivered within 500 milliseconds of each other, and preferably the gradient field created by each defibrillation pulse in the heart of the patient is greater than 4 volts per centimeter.

Figure 12:
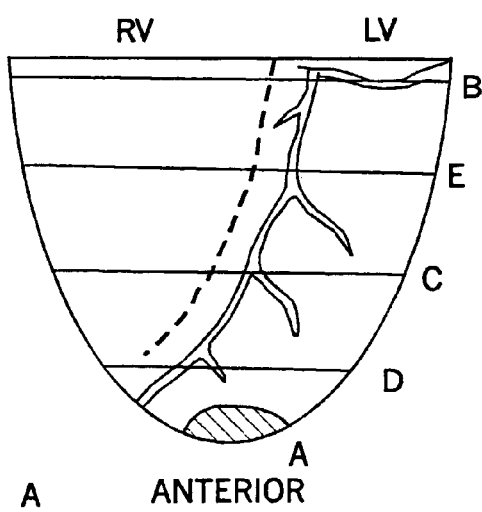
FIG. 12 schematically illustrates a technique for lowering ventricular defibrillation voltage that implements the technique illustrated in FIGS. 11A–C.

The foregoing method of reducing shock voltage may be implemented in techniques other than atrial defibrillation. For example, FIG. 12 schematically illustrates a technique for lowering ventricular defibrillation threshholds during open-chest cardiac surgery with an array of three or more epicardial electrodes. The particular electrode array of FIG. 12 is similar to the array of FIG. 11C. Such a system decreases the voltage needed for defibrillation in the operating room, which could decrease the damaging effects associated with large defibrillation shocks. Since the electrodes in FIG. 12 are placed on the epicardium, they will not have as much effect on the shock potential gradient field in the ventricular septum as they will in the ventricular free walls. A modification of this system to increase the potential gradient in the septum is, accordingly, to add an additional electrode (F) place in the right ventricular cavity against the inter-ventricular septum, optionally as part of a catheter. Then, in addition to the various possible concurrent shock sequences through electrodes A to E, one or more shocks could be delivered from electrode F to some or all of electrodes A to E. Systems for implementing such methods can be provided with the necessary electrodes operably associated with a pulse generator configured or programmed to carry out the shock patterns described herein in accordance with known techniques.

Figure 17:
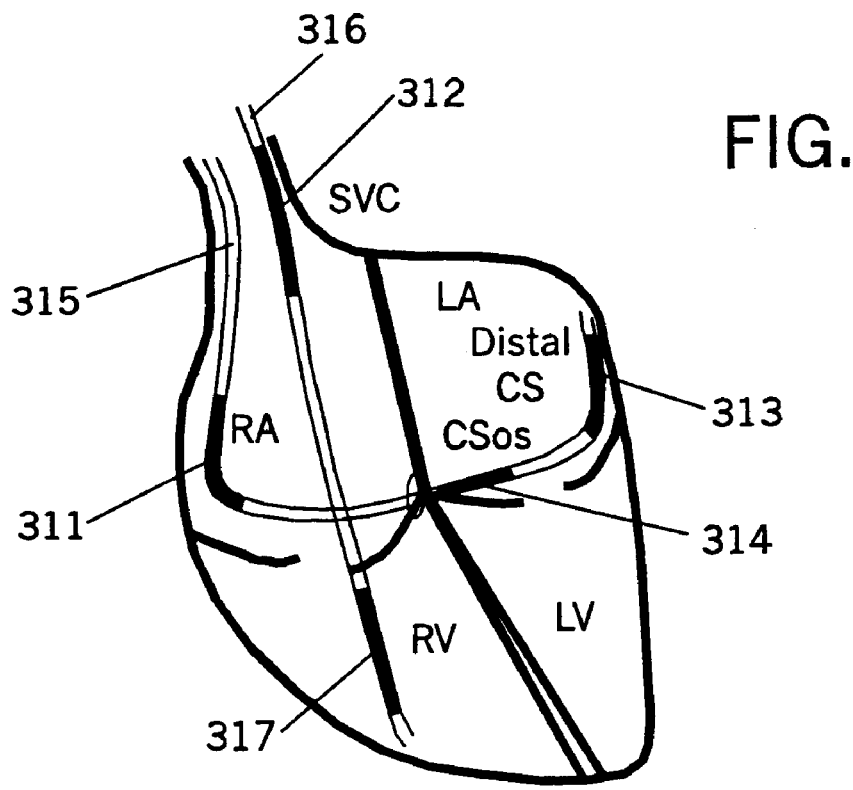
Figure 18:
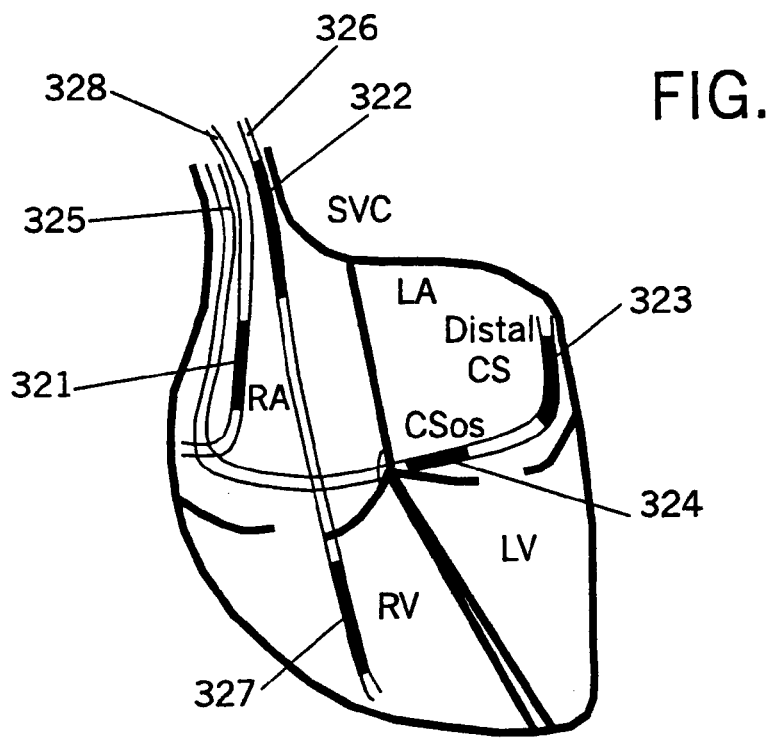

The implementation of the present invention in connection with a Bachmann's bundle electrode is further illustrated in connection with FIGS. 16–18, where "RA" means right atrium, "RV" means right ventricle, "LA" means left atrium, "LV" means left ventricle, "SVC" means superior vena cava, "CSos" means ostium of the coronary sinus, and "Distal CS" means distal coronary sinus. Therapeutic pulses and other electrodes may be implemented as described above in connection with atrial septum electrodes.

Figure 16:
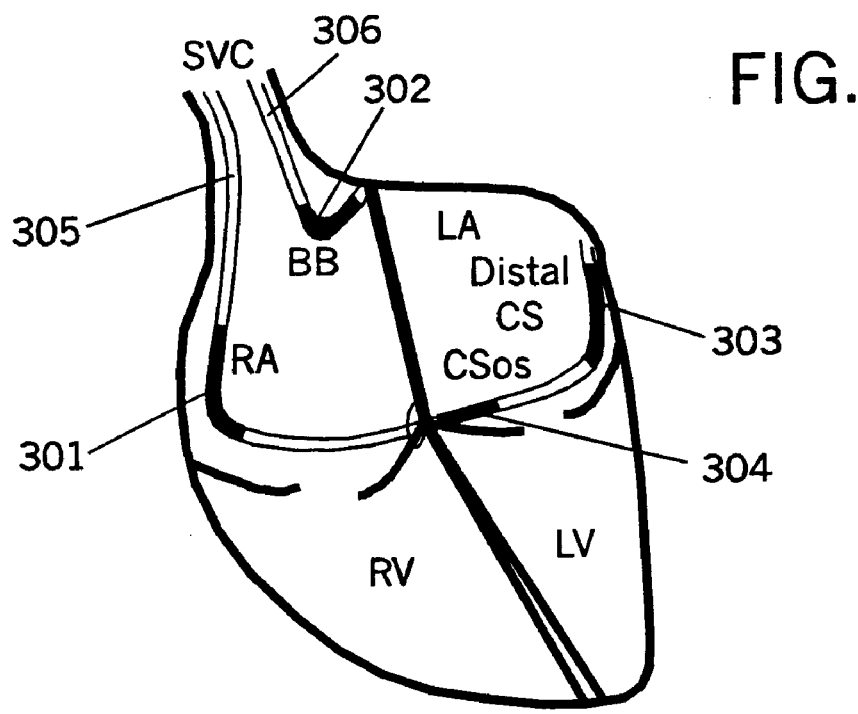

For example, as shown in FIG. 16, defibrillation may be carried out with two shocks or defibrillation pulse, with one of the shocks delivered from an electrode 301 at the right atrium to the distal coronary sinus 303, and the other delivered from an electrode 302 at Bachmann's bundle, near or adjacent the anterior-superior insertion of the atrial septum, to an electrode 304 in or adjacent the coronary sinus ostium (os), near the posterior-inferior insertion of the atrial septum. The electrode at the os of the coronary sinus can be on the same catheter 305 that contains the electrode in the distal coronary sinus. The electrode at Bachmann's bundle can be on its own lead 306. The right atrial electrode can either be on its own lead, or on the lead passing into the coronary sinus.

The first of the two shocks can be either through the right atrial to distal coronary sinus electrodes or through the Bachmann's bundle to coronary sinus os electrodes. The voltage of the second shock can be (1) equal to the trailing edge voltage of the first shock as from a single capacitor, (2) equal to the leading edge voltage of the first shock, as would occur if each shock were delivered from a different capacitor charged to the same voltage, or (3) with the voltage of the second shock some other fraction of the voltage of the first shock, as could be performed with two capacitors charged to different voltages. All three of these cases can be delivered from a single capacitor bank by using an electronic circuit to cause the voltages of the first and second shock to be the desired values. For example, atrial defibrillation with such electrode configurations may be carried out with less than 200 or 300 volts, while the capacitor bank in an atrial-ventricular defibrillator can be charged to approximately 800 volts since this voltage is required for ventricular fibrillation. An electronic control circuit can shape the waveform delivered from the 800 voltcapacitor to be almost any desired shape for two different shocks each of which are less than 200 or 300 volts.

Note that the insertion of the superior vena cava into the right atrium is near Bachmann's bundle. Therefore another shock configuration is to substitute an electrode in the superior vena cava for the electrode at Bachmann's bundle, e.g., to stimulate Bachmann's bundle. The advantage of this configuration for an atrial-ventricular defibrillator is that the superior vena cava electrode is already present for delivering shocks to halt ventricular arrhythmias. Possible lead configurations using the electrode in the superior vena cava are shown in FIGS. 17–18. As illustrated in FIG. 17, such an embodiment may comprise a first catheter 315 carrying a right atrium electrode 311, a coronary sinus os electrode 314, and a distal coronary sinus electrode 313 as described above, and a second cathter or lead 316 carrying a superior vena cava electrode 312 and an optional right ventricle electrode 317 (which may be used for atrial or ventricular defibrillation). Still another embodiment, as illustrated in FIG. 18, an embodiment may comprise a first catheter 325 carrying a coronary sinus os electrode 324 and a distal coronary sinus electrode 323 as described above, a second catheter or lead 326 carrying a superior vena cava electrode 322 and an optional right ventricle electrode 327 (which may be used for atrial or ventricular defibrillation), and a third catheter or lead 328 carrying a right atrial electrode 321 (which third catheter 328 may or may not be attached to first catheter 325 in the manner described in connection with FIG. 10 above). One preferred embodiment of the shocks would be right atrium to distal coronary sinus, followed by superior vena cava to coronary sinus ostium. Another configuration would be with these two shocks in reverse sequence.

Figure 19:
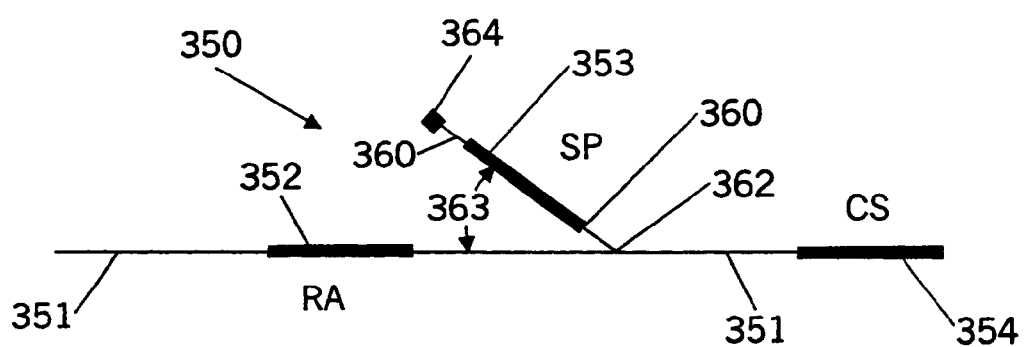

Another catheter device that may be used in carrying out the present invention is a flexible, two-pronged catheter 350, which may be used for (among other things) situating electrodes such as defibrillation electrodes in the right atrium, the coronary sinus, and along the right side of the atrial septum (or Bachmann's bundle). The device, schematically illustrated in FIG. 19, is comprised of a primary catheter body 351 that has lead body (preferably coil) electrodes 352, 353, 354; the distal electrode 354 may be used for situation or insertion into the coronary sinus, and the proximal electrode 352 may be used for situation in the right atrijum. The electrode 353 (SP) carried by an appendage catheter body 360 connected to the primary catheter body 351, may be used for situation along the right side of the atrial septum or Bachmann's bundle, and is connected to the primary catheter body mid portion, preferably between the electrodes 352, 354, and in one embodiment approximately half way between electrodes 352 and 354. This SP electrode may take one of several forms. The appendage catheter body 360 is connected to the primary catheter body 351, at a junction portion 362 that has a memory and corresponding elasticity such that the angle 363 between the primary catheter body 351 and the appendage catheter body 353 is about 30, 50 or 70 to 120, 140 or 160 (most preferably about 90) degrees off of the primary catheter body. But, the elongate connector has elasticity at its cfonnection portion with the primary catheter such that the SP electrode may be bent back in line (substantially parallel) with the primary catheter. In this manner, the SP electrode may be bent along the primary catheter for transvenous situation of the catyheter system into the heart, for example by insertion through an introducer tube or guide. For extraction, the SP elongate member may also be elastically bent back in the opposite direction along the axis of the primary catheter toward the CS electrode.

The SP electrode may take one of several forms. A simple embodiment is a lead-body coil electrode, as found in ICD lead-body defibrillation electrodes. In this embodiment the inner diameter of the introducer required to situate the catheter system must be equal to at least the sum of the diameters of the SP coil and primary catheter. In an alternate embodiment, the SP electrode may be a relatively flat mesh electrode. This flat mesh electrode may be of a length as desired (e.g., 1 to 6 cm). Its width may be up to (for example) the circumference of the primary catheter. Being pliable, during placement of the catheter system, the SP electrode may be bent back over the proximal side of the primary catheter, and the SP electrode may be "wrapped" around the primary catheter, thereby requiring an introduce with an inner diameter that is not substantially greater than that which would be employed without the SP member.

While the connecting portion of the SP member attchement to the primary catheter has elasticity, the primary catheter body has rotational stiffness so that, once in the general vicinty, the prximal end of the catheter may be rotated to optimize the position of the SP electrode. Further, the material connecting the SP elongate member to the primary catheter may be made of a memory alloy, polymer, or composite thereof, or the like, such that it maintains the desired angle as noted above relative to the long axis of the primary catheter. Also, an optional pacing tip electrode 364 may be placed at the tip of the SP elongate member, so that the pacing of the atrial septum or Bachmann's Bundle may be performed.

The present invention may be implemented in combination with, or employing the features of, numerous additional methods and systems for the defibrillation and cardioversion of a patient's heart, including but not limited to those disclosed in U.S. Pat. No. 6,006,131 to Cooper et al.; U.S. Pat. No. 6,002,962 to Huang et al.; U.S. Pat. No. 5,987,354 to Cooper et al.; U.S. Pat. No. 5,978,705 to Ideker et al.; U.S. Pat. No. 5,978,704 to Ideker et al. U.S. Pat. No. 5,509,925 to Adams; U.S. Pat. No. 5,630,834 to Bardy; and U.S. Pat. No. 5,476,499 to Hirschberg. The disclosures of all U.S. Patent references cited herein are to be incorporated herein by reference in their entirety.

The present invention is further illustrated in the experimental examples set forth below.

EXAMPLES

Reduction of Atrial Defibrillation Threshold With an Interatrial Septal Electrode This example demonstrates that an electrode configuration with an interatrial septal electrode placed approximately midway between the right atrial appendage and coronary sinus electrodes increases the potential gradient in this region and thus lowers the atrial defibrillation threshold (ADFT).

I. METHODS

All studies were performed in accordance with the guidelines established in the Position of the American Heart Association on Research Animal Use adopted by the American Heart Association on Nov. 11, 1984.

Of 11 adult sheep, 8 (41±6 kg, heart mass 217±8 g) completed the experimental protocol; only data from these 8 animals were compiled.

Animal Preparation. As a preanesthetic agent, a 1-to-1 mixture of tiletamine and zolazepam (8–10 mg/kg) was given intramuscularly. About 10 minutes later, thiopental (2–6 mg/kg) was administered as a slow intravenous bolus. The animal was laid in a dorsally recumbent position on a fluoroscopy table, intubated, and placed on a volume-cycled ventilator (tidal volume: 15–20 ml/kg) with a 4% isoflurane/oxygen mixture at a rate of 8–12 breaths per minute. The isoflurane concentration was decreased to 1.5–3.5% to maintain a deep surgical plane of anesthesia. Ventilator settings were adjusted as necessary to correct for respiratory acidosis or hypoxemia. Intravenous fluids (Lactated Ringer's solution) were infused throughout the experiment with supplemental electrolytes as needed as determined by serial blood gas and chemistry analyses conducted every 30–60 minutes.

An 8 Fr. sheath was placed in the left femoral artery percutaneously for continuous arterial pressure monitoring. The animal was instrumented for lead II ECG and esophageal temperature monitoring. A heated water blanket was used to maintain body temperature at 37±1° C. Neuromuscular blockade was achieved with a 1 mg/kg succinylcholine chloride intravenous bolus followed by an intravenous drip (5–8 mg/min) for maintenance, depending upon neuromuscular tone. At all times, an external defibrillator with external paddles was available in the event of non-perfusing ventricular tachyarrhythmia.

Defibrillation Catheter Placement. All catheters were positioned transvenously under fluoroscopic guidance. Through a jugular vein, a defibrillation lead (Perimeter #7109, Guidant Corp., St. Paul, Min.) with a distal 6-cm long electrode was situated with its coil electrode in the distal coronary sinus (CS) along the left lateral heart and its tip under the left atrial appendage. Care was taken to not place this lead in the persistent superior vena cava, which is present in this species. A modified quadripolar catheter (Mansfield EP-Boston Scientific Corp., Watertown, Mass.) with a 3.5-cm-long coil electrode 1 cm proximal to the catheter tip was positioned in the right atrial appendage (RAA) through the left femoral vein. The coil electrode was laid along the superior wall of the RAA. The bipolar tip of this catheter was used for the burst-pacing induction of AF. Another two 3.5-cm-long coil electrode catheters were also placed in the main and left pulmonary artery (PA) and lower right atrium (LRA), respectively. The LRA electrode was positioned at the junction of right atrium and inferior vena cava.

A custom-made 6-cm coil electrode that served as the interatrial septal electrode (SP) was constructed along a catheter; the distal end of the electrode was 3 cm from the catheter tip. It was situated through a trans-septal procedure. An 8 Fr. Mullins sheath was advanced into the right atrium through the right femoral vein over a 0.038" guide wire. Then, a Brockenbrough needle replaced the guide wire and was displaced through the atrial septum, usually under LAO projection. Confirmation of left atrial catheterization was made by measurement of oxygen saturation of blood withdrawn through the Brockenbrough needle and with contrast injection into the left atrium during fluoroscopy. A stiff 0.038" guide wire was positioned in the left atrium through the sheath. The Mullins sheath was then withdrawn over the wire, leaving the wire in the left atrium. Next, an 11 Fr. guide sheath was advanced over the wire and into the left atrium. After withdrawal of the dilator and guide wire, the septal electrode was inserted into the left atrium through the guide sheath. The tip of the septal electrode catheter was placed against the lateral wall of left atrial appendage. About ⅔ of the electrode was in the left atrium and ⅓ in the right atrium. After the septal electrode was in position, 1000 units of heparin were given intravenously every hour.

Additionally, a three-electrode defibrillation catheter (Endotak DSP, Guidant Corp., St. Paul, Min.) was introduced into the right ventricle through the other jugular vein; the two lead-body coil electrodes from this catheter were situated in the right ventricle (RV) and superior vena cava (SVC). The tip electrode from this catheter was used for ventricular pacing. A three-wire subcutaneous array (SQA) was inserted over the left side of the heart. In the event of ventricular tachyarrhythmias, the electrode configuration for ventricular defibrillation was RV as the first phase anode with CS, SVC and SQA electrically common as the first phase cathode (RV→CS+SVC+SQA).

Induction of Atrial Fibrillation. To allow AF to be maintained, acetyl-β-methylcholine chloride (Sigma Chemicals Co., St Louis, Mo.) was continuously infused into the pericardium. The pericardial space was approached percutaneously under fluoroscopic guidance with a 3-inch-long 16-gauge needle from just inferior to the right subxiphoid position with the animal turned about 20 degrees toward the right side. When the needle was confirmed to be within the pericardial space by contrast injection, a guide wire was gently inserted within the needle into the pericardial space. The pericardial location for the guide wire was confirmed by inability to move it outside the fluoroscopic image of the heart silhouette. After removal of the needle, a 6 Fr. sheath was advanced into the pericardial space over the wire. After flushing with acetyl-β-methylcholine chloride, a 4 Fr. pigtail catheter was inserted through the sheath. Typically, the catheter tip was advanced to near the left atrial appendage and the sheath was removed.

Acetyl-β-methylcholine chloride solution (1 g/250 ml saline) was infused at a rate of 20 μL/min using a microinfuser. Burst pacing used to induce AF consisted of 2-ms stimuli delivered at intervals of 30–60 ms. AF was defined as irregular rapid atrial activity with an irregular ventricular response on the ECG. Blood pressure and heart rate were recorded before and 20 min after acetyl-β-methylcholine infusion.

Defibrillation Waveforms and Lead Configurations. Once acetyl-β-methylcholine chloride was infused long enough to support AF maintenance of >10 minutes (typically ~20 minutes), the defibrillation protocol was begun. The waveform generation system has been described previously (R. Cooper et al., Circulation. 1997;96:2693–2700). Briefly, a monophasic waveform was produced by a programmable defibrillator (HVS-02, Ventritex, Inc). This monophasic waveform was divided into a biphasic, truncated-exponential waveform by a high-voltage, cross-point switch; for sequential shocks, two biphasic, truncated-exponential waveforms were created with the use of an additional pair of cross-point switches. Each biphasic waveform had a first-phase duration of 3 ms and a second-phase duration of 1 ms. The interval between each phase of the biphasic waveforms and between the two biphasic waveforms of sequential shocks was 20 μsec. Because all stimuli (single or sequential shocks) were produced from the output of one defibrillator, all phases of the waveforms exhibited decaying voltage from a single capacitor, in which the trailing-edge voltage of each preceding phase was equal to the leading-edge voltage of the succeeding phase.

In each animal, the ADFTs of five test configurations were determined (Table 1). Three configurations utilizing the septal electrode were named A1, A2 and A3. The two others were named B and C, respectively. The order of determining the test-configuration ADFTs was randomized in each animal as follows. The order among A, B and C was initially randomized, and then the order of A1, A2 and A3 (within A) was randomized. The ADFTs of the configurations utilizing the septal electrode were measured consecutively in order to obviate the need for repositioning this electrode. During the ADFT testing of any configuration, passive electrodes not delivering any shock for that configuration were removed. To minimize the likelihood of ventricular tachyarrhythmia induction, shock delivery was synchronized to right-ventricular pacing, which triggered the Ventritex defibrillator and cross-point switches via custom software on a Macintosh Computer. The cycle length of this pacing was 250–400 ms, depending on the ventricular rate during AF. Shocks were delivered 20 ms after the 8$^{th}$ pacing pulse.

TABLE 1

Test Configurations

| | First Shock | | Second Shock | | Biphasic |
|---|---|---|---|---|---|
| | Anode | Cathode | Anode | Cathode | Waveform |
| A1 | RAA + CS | SP | | | Single |
| A2 | RAA | SP | CS | SP | Sequential |
| A3 | CS | SP | RAA | SP | Sequential |
| B | RAA | CS | | | Single |
| C | RAA | CS | LRA | PA | Sequential |

RAA: right atrial appendage, CS: coronary sinus, SP: atrial septum, LRA: low right atrium, PA: pulmonary artery.

The ADFT of each test configuration was determined using a multiple-reversal method with an initial starting peak voltage of 100 V and step sizes of 40/20/10 V. If the initial shock failed, the next and subsequent shock voltages were increased by 40 V until a shock succeeded. Following the first shock that successfully terminated AF, the voltages of subsequent shocks were decreased by 20 V until a shock failed. Then the shock voltages were increased by 10 V until a shock succeeded again. Conversely, if the initial shock succeeded, subsequent shock voltages were decreased by 40 V until a shock failed. Then shock voltages were increased by 20 V until a shock succeeded, after which shock voltages were decreased by 10 V until a shock failed again. The last successful shock of the third reversal was deemed the ADFT of the test configuration. Before starting the defibrillation protocol, 3–5 test shocks were given. All test shocks were delivered after inducing AF and allowing it to be sustained 1 minute. When a test shock failed, a rescue shock of 200–300 V was given. A 1–2 min period of sinus rhythm was allowed before the next induction of AF.

Data Acquisition. The leading-edge (peak) voltage and current of each test shock were recorded, and the impedance and delivered energy of each shock were computed by a waveform analyzer (DATA 6100, Data Precision).

Postmortem Examination. After the completion of data collection, euthanasia was induced with an intravenous bolus of potassium chloride. The chest was opened and the location of the electrodes of the last test configuration was confirmed by palpation through the heart walls. The heart was then removed. The great vessels were trimmed to the point of insertion into each cardiac chamber, and the pericardium was removed. The mass of the heart was determined.

Statistical Analysis. Results are expressed as the mean±SD. The overall effect of the 5 test configurations on each ADFT characteristic was tested by repeated-measures ANOVA. Pair-wise differences in measures between the 5 configurations were tested by paired t tests. A value of $P<0.05$ was considered significant.

II. RESULTS

Reproducible, sustained AF could be induced in all animals. The ventricular rate in sinus rhythm before and 20 min after administration of acetyl-β-methylcholine was similar (112±8 vs. 109±11 beat/min, respectively, P=NS). The drug significantly lowered the sinus-rhythm systolic/diastolic blood pressure, however (107±8/83±4 vs. 84±7/62±5 mmHg, $P<0.05$). During AF, the ventricular rate varied from 80 to 178 beat/min (131±36 beat/min). After successful test shocks, sinus rhythm usually recovered quickly (<1.5 sec). In 1 sheep with a long sinus recovery time (>2–4 sec), temporary post-shock atrial pacing was performed.

Figure 13:
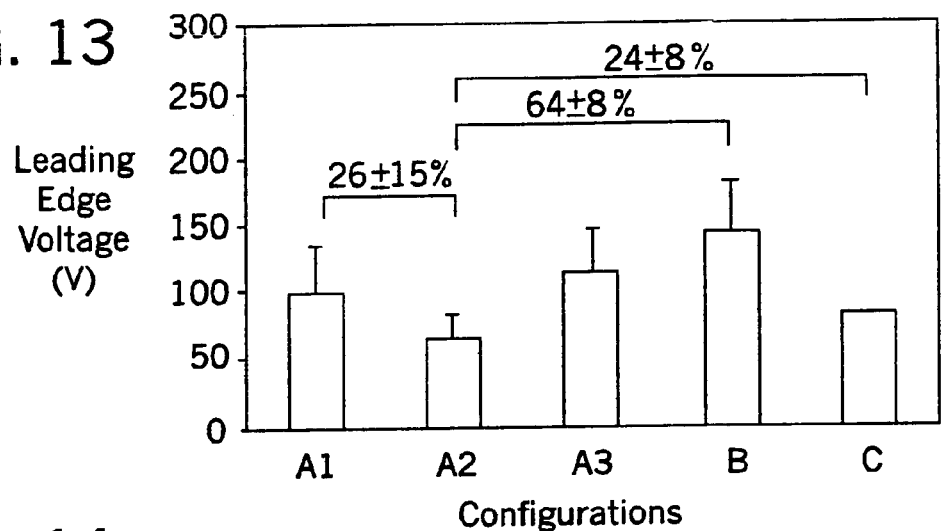
FIG. 13 shows the ADFT leading edge voltage in experimental animals used to demonstrate the instant invention. The leading edge voltage of configuration A2 is significantly lower than the others (number shows the percent lower).

Leading Edge Voltage. The ADFT leading-edge-voltage of the 5 configurations is shown in FIG. 13. The ADFT leading-edge-voltage of configuration A2 (RAA→SP/ CS→SP; 71±16 V) was significantly lower than each of the other 4 configurations (A1: 102±36 V; A3: 121±34 V; B: 156±38 V; and C: 96±29 V). The ADFT leading-edge-voltage of configuration B (RAA→CS) was significantly higher than the other 4 configurations.

Figure 14:
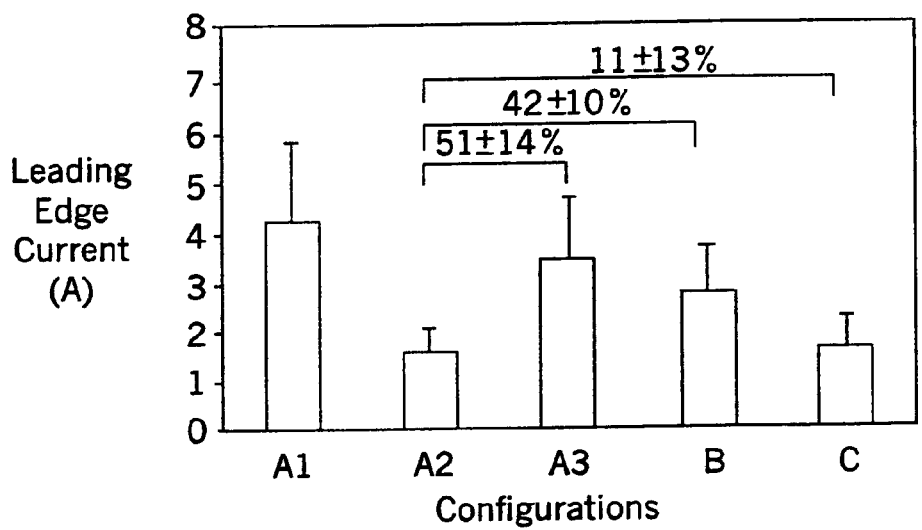
FIG. 14 shows the ADFT leading edge current in experimental animals used to demonstrate the instant invention. The leading edge current of configuration A2 is significantly lower than the others (number shows the percent lower).

Leading Edge Current. The ADFT leading-edge-current is shown in FIG. 14. The ADFT leading-edge-current of configuration A2 (1.68±0.48 A) was significantly lower than that of the other 4 configurations A1, A3, B and C (A1: 4.32±1.59 A; A3: 3.61±1.28 A; B: 2.99±1 A; and C: 1.92±0.65 A). The ADFT leading-edge-current of configuration C was lower than that of configurations A3 and B. The leading-edge-current ADFT of configuration A1, which was the sum of the currents of two pathways: RAA→SP and CS→SP, was higher than that of configurations A2, B and C but not configuration A3.

Impedance. The impedances of the test configurations are shown in Table 2. Impedances of the same pathway in different test configurations were not significantly different. Configuration A1 exhibited the lowest impedance, which was approximately the reciprocal of the sum of the reciprocal impedances of its two pathways (RAA→SP and CS→SP) as estimated from individual shocks across these pathways during sequential shocks.

Figure 15:
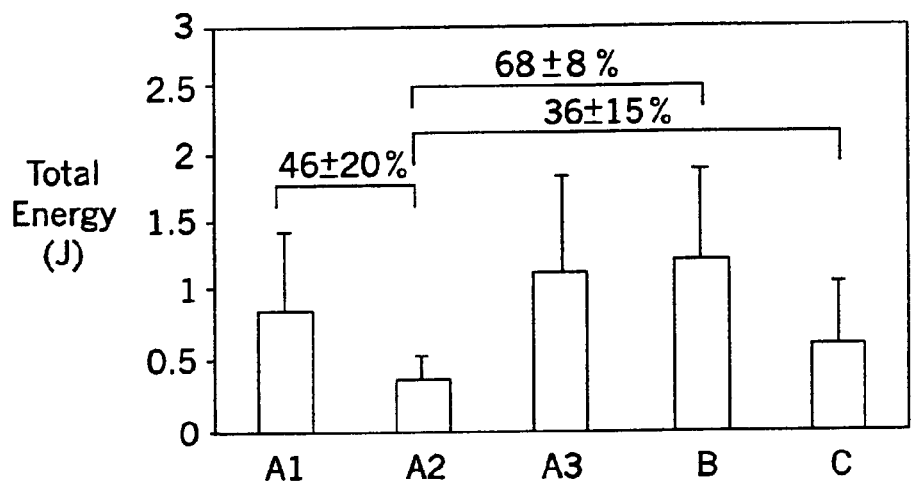
FIG. 15 shows the ADFT total shock energy in experimental animals used to demonstrate the instant invention. The shock energy of configuration A2 is significantly lower than the others (number shows the percent lower).

Shock Energy. The ADFT shock-energy of the 5 configurations is shown in FIG. 15. Configuration A2 had a significantly lower ADFT shock-energy than each of the other 4 test configurations (A2: 0.39±0.17 J vs. A1: 0.86±0.59 J, A3: 1.16±0.72 J, B: 1.27±0.67 J, and C: 0.68±0.46 J; P<0.05 for each comparison). The ADFT shock-energy of configuration A2 was lower than that of configurations A1, A3, B and C by 46±20%, 63±14%, 68±8%, and 36±15%, respectively. Configuration C had a lower ADFT shock-energy than configurations A1, A3 and B (P<0.05 for each comparison). Compared with configuration B, configuration C reduced shock energy by 50±9%. Configuration A1 had a lower ADFT shock-energy than configuration B (37±15% lower, P<0.05), but not than configuration A3. The difference in ADFT shock-energy between configurations A3 and B was not significant.

TABLE 2

Impedances of all the current pathways

| | | Current Pathways | Impedance($\Omega$) |
|---|---|---|---|
| A1 | Single | RAA + CS → SP | 25 ± 3 |
| A2 | First | RAA → SP | 46 ± 3 |
| | Second | CS → SP | 34 ± 4 |
| A3 | First | CS → SP | 35 ± 4 |
| | Second | RAA → SP | 45 ± 4 |
| B | Single | RAA → CS | 54 ± 6 |
| C | First | RAA → CS | 54 ± 7 |
| | Second | LRA → PA | 49 ± 4 |

RAA: right atrial appendage, CS: coronary sinus, SP: atrial septum, LRA: low right atrium, PA: pulmonary artery.

While care must be used in directly extrapolating the results of this study to humans because of the particular pharmaceutical interventions employed. Nevertheless, this study demonstrates that, in an acute sheep model of sustained AF, atrial defibrillation configurations utilizing an additional electrode at the interatrial septum were more efficacious than the present standard configuration by which cardioversion is achieved with RAA→CS. The ADFT shock-energy of RAA+CS→SP was 37±15% lower, and sequential shock configuration RAA→SP/CS→SP was 68±8% lower than that of RAA→CS.

The foregoing is illustrative of the present invention, and is not to be construed as limiting thereof. The invention is defined by the following claims, with equivalents of the claims to be included therein.

That which is claimed is:

1. An implantable system for the defibrillation of the atria of a patient's heart, said system comprising:
   a first atrial defibrillation electrode configured for stimulating Bachmann's bundle and for positioning on or adjacent Bachmann's bundle along the superior aspect of the atrium and adjacent to the atrial septum;
   a second atrial defibrillation electrode which together with said first atrial defibrillation electrode provides a pair of atrial defibrillation electrodes; and
   a pulse generator operatively associated with said pair of atrial defibrillation electrodes for delivering an atrial defibrillation pulse.

2. The implantable system according to claim 1, wherein said first atrial defibrillation electrode is carried by a first catheter, said first catheter configured for insertion into the right atrium of said heart without extending into the right ventricle of said heart.

3. An implantable system according to claim 1, wherein the electrode is configured to be positioned within a trans-septal puncture in the atrial septum or in Bachmann's bundle.

4. An implantable system according to claim 1, wherein said first atrial defibrillation electrode is carried by a first catheter, said first catheter has a distal end portion and a terminal screw connected to the distal end portion, whereby said first electrode may be fixed to said atrial septum or Bachmann's bundle with said terminal screw.

5. An implantable system according to claim 1, wherein said first atrial defibrillation electrode is carried by a first catheter, and said first catheter has a distal end portion and a retractable hook connected to said distal end portion, whereby said first electrode may be fixed to the atrial septum or Bachmann's bundle with said hook.

6. An implantable system according to claim 1, wherein said first atrial defibrillation electrode is carried by a first catheter, said first catheter having a distal end portion and an expandable member connected to said distal end portion, with said first electrode connected to said expandable member.

7. An implantable system according to claim 1, further comprising a first catheter configured for carrying the first atrial defibrillation electrode and a second catheter configured for insertion through the coronary sinus and into a vein on the surface of the left ventricle of the heart, wherein said second electrode is connected to the second catheter.

8. An implantable system according to claim 1, further comprising an implantable housing having an external surface portion, with said pulse generator contained within the housing, and with the second electrode connected to the external surface portion of the housing.

9. A method for the defibrillation of the atria of a patient's heart, said method comprising:
   positioning a first atrial defibrillation electrode on or adjacent Bachmann's bundle along the superior aspect of the atrium and in or adjacent to the atrial septum for stimulating Bachmann's bundle;
   positioning a second atrial defibrillation electrode to provide a pair of atrial defibrillation electrodes together with said first atrial defibrillation electrode; and
   administering an atrial defibrillation pulse through said pair of atrial defibrillation electrodes.

10. The method according to claim 9, wherein said first atrial defibrillation electrode is carried by a first catheter, and said first catheter is inserted into the right atrium of said heart without extending into the right ventricle of said heart.

11. The method according to claim 9, wherein the said first atrial defibrillation electrode is positioned within a trans-septal puncture in the atrial septum or in Bachmann's bundle.

12. The method according to claim 9, wherein said first atrial defibrillation electrode is carried by a first catheter, said first catheter has a distal end portion and a terminal screw connected to the distal end portion, and said first atrial defibrillation electrode is fixed to the atrial septum with said terminal screw.

13. The method according to claim 9, said first atrial defibrillation electrode is carried by a first catheter, and said first catheter has a distal end portion and a retractable hook connected to said distal end portion, and said first atrial defibrillation electrode is fixed to the atrial septum or Bachmann's bundle with said hook.

14. The method according to claim 9, said first atrial defibrillation electrode is carried by a first catheter, said first catheter having a distal end portion and an expandable member connected to said distal end portion, with said first electrode connected to said expandable member, and said first atrial defibrillation electrode is positioned by expanding said expandable member.

15. The method according to claim 9, wherein said first atrial defibrillation electrode is carried by a first catheter, the method further comprising inserting a second catheter through the coronary sinus and into a vein on the surface of the left ventricle of the heart, wherein said second electrode is connected to said second catheter.

16. The method according to claim 9, wherein first said atrial inserting a first catheter and a second catheter carrying said pair of atrial defibrillation electrodes into the patient, with said first catheter connected to said second catheter inside the heart.

17. The method according to claim 16, wherein said second catheter is positioned in the right ventricle or coronary sinus of said heart.

18. An implantable system for the defibrillation of the atria of a patient's heart, said system comprising:

a first catheter carrying a first atrial defibrillation electrode configured for stimulating Bachmann's bundle and for positioning on or adjacent Bachmann's bundle along the superior aspect of the atrium and adjacent to the atrial septum;

a second catheter connected to said first catheter at a junction configured for placement inside the heart, the second catheter carrying a second atrial defibrillation electrode which together with said first atrial defibrillation electrode provides a pair of atrial defibrillation electrodes; and a pulse generator operatively associated with said pair of atrial defibrillation electrodes for delivering an atrial defibrillation pulse.

19. An implantable system according to claim 18, wherein said second catheter is configured for positioning in the right ventricle or coronary sinus of said heart.

20. Method for the defibrillation of the atria of a patient's heart, said method comprising:

inserting a first catheter carrying a first atrial defibrillation electrode and a second catheter carrying a second atrial defibrillation electrode into the heart, with said first catheter connected to said second catheter at a junction inside the heart and said first atrial defibrillation electrode and said second atrial defibrillation electrode together providing a pair of atrial defibrillation electrodes;

positioning the first atrial defibrillation electrode on or adjacent Bachmann's bundle along the superior aspect of the atrium and in or adjacent to the atrial septum for stimulating Bachmann's bundle; and administering an atrial defibrillation pulse through said pair of atrial defibrillation electrodes.

21. The method according to claim 20, further comprising inserting the second catheter through the coronary sinus and into a vein on the surface of the left ventricle of the heart.

22. The method according to claim 20, wherein said second catheter is positioned in the right ventricle or coronary sinus of said heart.

* * * * *

UNITED STATES PATENT AND TRADEMARK OFFICE
CERTIFICATE OF CORRECTION

PATENT NO. : 6,804,553 B2
DATED : October 12, 2004
INVENTOR(S) : Zheng et al.

It is certified that error appears in the above-identified patent and that said Letters Patent is hereby corrected as shown below:

Column 21,
Lines 16-17, should read -- 16. The method according to claim 9, further comprising inserting a first catheter and a second catheter carrying --

Signed and Sealed this

Fifteenth Day of March, 2005

JON W. DUDAS
*Director of the United States Patent and Trademark Office*